United States Patent [19]

Dryden et al.

[11] Patent Number: 4,480,112

[45] Date of Patent: Oct. 30, 1984

[54] METHOD AND INTERMEDIATES FOR PRODUCING α-L-ASPARTYL-L-PHENYLALANINE

[75] Inventors: Hugh L. Dryden, Deerfield; John B. Hill, Woodstock, both of Ill.

[73] Assignee: G. D. Searle & Co., Skokie, Ill.

[21] Appl. No.: 580,912

[22] Filed: Feb. 16, 1984

Related U.S. Application Data

[62] Division of Ser. No. 506,465, Jun. 20, 1983.

[51] Int. Cl.$^3$ ............... C07C 101/20; C07D 307/60
[52] U.S. Cl. ........................... 549/478; 562/571; 549/477
[58] Field of Search ............. 562/571; 549/477, 478

[56] References Cited

U.S. PATENT DOCUMENTS

| | | | |
|---|---|---|---|
| 2,200,220 | 5/1940 | Reppe et al. | 562/430 |
| 3,462,460 | 8/1969 | Kollonitsch | 562/571 |
| 3,933,781 | 1/1976 | Bachman et al. | 260/112.5 R |
| 4,173,562 | 11/1979 | Bachman et al. | 260/112.5 R |

OTHER PUBLICATIONS

*Chemical Abstracts,* 64, (1966), Abst. No. 19754c.
Carlo Di Bello et al., *J. Chem. Soc.,* (C), 350, (1969).

*Primary Examiner*—Delbert R. Phillips
*Assistant Examiner*—F. T. Moezie
*Attorney, Agent, or Firm*—Steven M. Odre; John J. McDonnell

[57] ABSTRACT

This invention encompasses a method and intermediates for preparing a commercial sweetening agent, α-L-aspartyl-L-phenylalanine methyl ester. The process involves reacting L-aspartic acid with diketene to form N-acetoacetyl-L-aspartic acid which is converted to N-acetoacetyl-L-aspartic anhydride by reaction with acetic anhydride. N-acetoacetyl-L-aspartic anhydride is reacted with L-phenylalanine methyl ester to provide N-acetoacetyl-α-L-aspartyl-L-phenylalanine methyl ester which is converted to α-L-aspartyl-L-phenylalanine methyl ester by reaction with hydroxylamine hydrochloride.

2 Claims, No Drawings

METHOD AND INTERMEDIATES FOR PRODUCING α-L-ASPARTYL-L-PHENYLALANINE

This is a division of application Ser. No. 06/506,465, filed June 20, 1983.

BACKGROUND OF THE INVENTION

α-L-aspartyl-L-phenylalanine methyl ester is a sweetening agent which is about 200 times sweeter than sucrose. The compound and its uses are extensively taught in U.S. Pat. Nos. 3,492,131; 3,642,491; and 3,780,189. A variety of methods for the economical synthesis of α-L-aspartyl-L-phenylalanine are known, for example, U.S. Pat. Nos. 3,933,781 and 4,173,562 describe the use of N-protected-L-aspartic anhydride in preparing α-L-aspartyl-L-phenylalanine methyl ester.

Chem Abstracts 64 19754C (1966) describes acetoacetyl derivatives of glycine, alanine, leucine, threonine, methionine and tryptophan made from the reaction of the corresponding amino acid with diketene. The acetoacetyl derivative of leucylglycine methyl ester is described in Tetrahedron Letters 10, 605-608 (1965). J. Chem. Soc (C), 350, (1969) describes the preparation of N-acetoacetylvaline and N-acetoacetylvalylvaline from valine and valylvaline respectively and diketene.

BRIEF DESCRIPTION OF THE INVENTION

The present invention involves a high yield large scale synthesis of α-L-aspartyl-L-phenylalanine methyl ester.

The preferred embodiment of the invention is illustrated in Scheme I.

SCHEME 1

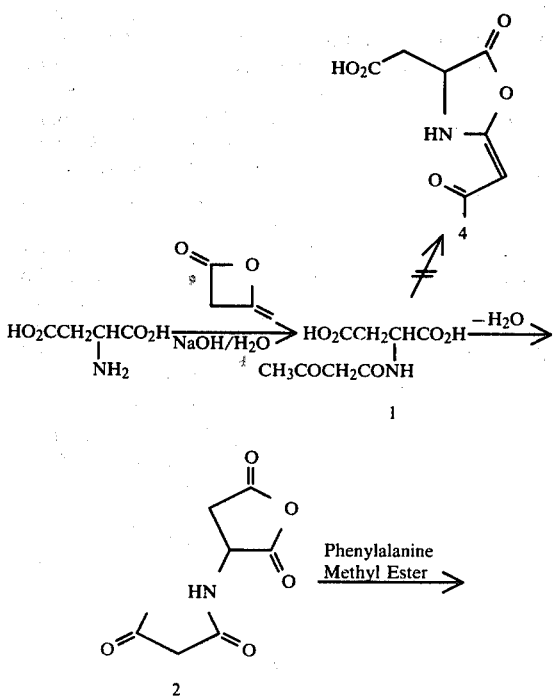

-continued
SCHEME 1

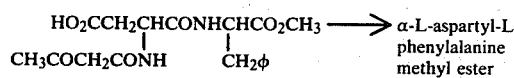

It has been discovered that diketene selectively reacts with the amino group of aspartic acid in high yield even though two carboxylic acid groups are present in aspartic acid. This reaction is conducted in basic solution, preferably basic methanol. The acetoacetyl group is stable during dehydrating procedures which form the anhydride and it is surprising that N-acetoacetyl L-aspartic anhydride is formed instead of the predicted oxazolidinone 4 in Scheme I. Acid anhydrides such as acetic anhydride and propionic acid anhydride and phosphorous trichloride are preferred dehydrating agents for converting N-acetoacetyl L-aspartic acid to N-acetoacetyl L-aspartic anhydride. The acetoacetyl group is removed with hydroxylamine salt such as the hydrochloride or sulfate under mild conditions in 99% yield without disturbing the ester and/or the free carboxyl group—a problem associated with removal of the formyl and acetyl group. For example, the formyl is removed by strong acids in aqueous methanol which causes esterification and hydrolysis.

Thus, the invention encompasses a method for preparing L-aspartyl-L-phenylalanine methyl ester comprising:

(a) reacting L-aspartic acid with diketene in basic solution at −10° C. to +20° C. to form N-acetoacetyl-L-aspartic acid.

(b) dehydrating N-acetoacetyl-L-aspartic acid with a dehydrating agent to form N-acetoacetyl-L-aspartic anhydride.

(c) reacting N-acetoacetyl-L-aspartic anhydride with L-phenylalanine methyl ester to form N-acetoacetyl-α-L-aspartyl-L-phenylalanine.

(d) removing the N-acetoacetyl group from N-acetoacetyl-α-L-aspartyl-L-phenylalanine by reaction with hydroxylamine hydrochloride.

The preferable dehydrating agents are acetic anhydride in acetic acid or ethyl acetate or phosphorous trichloride in ethyl acetate/acetic acid.

Novel intermediates of the invention are
N-acetoacetyl-L-aspartic acid
N-acetoacetyl-L-aspartic anhydride
N-acetoacetyl-α-L-aspartyl-L-phenylalanine

DETAILED DESCRIPTION OF THE INVENTION

The above named novel intermediates are shown in Scheme I as structures 1, 2 and 3, respectively. Free carboxylic acid groups in these compounds can be converted to the respective salts such as sodium, potassium, calcium and the like by reaction with the appropriate base. Thus reaction mixtures which contain compound 1, 2 or 3 whether as the free base or acid or base salts are within the scope of the invention.

EXAMPLES

N-acetoacetyl-L-aspartic acid

L-aspartic acid, 13.3 parts, was added to 100 parts by volume of 2N aqueous sodium hydroxide and the resulting solution was cooled to 0°–10° C. in an ice bath. Diketene, 8.4 parts, was added and the resulting two phase mixture was stirred for 2.5 hours at 0°–10° C. The homogeneous solution was washed twice with 100 parts by volume of ether and the aqueous layer was acidified with 16.6 parts by volume of concentrated hydrochloric acid. This solution was extracted three times with 100 parts by volume of ethyl acetate, the combined extracts were dried over sodium sulfate, filtered and the solvent evaporated under vacuum at 25°–30° C. to give 2.3 parts of N-acetoacetyl-L-aspartic acid, mp 127°–129.5° C.

Elemental analysis for $C_8H_{11}NO_6$: Calc. C, 44.24; H, 5.10; N, 6.45; Found C, 44.59; H, 5.24; N 6.10.

NMR (DMSO-D6): δ 2.18, 3H, s; 2.70, 2H,d; 3.38, 2H, s; 4.59, 1H, m; 8.40, 1H, m.

N-acetoacetyl-L-aspartic Anhydride 1.41 parts of N-acetoacetyl-L-aspartic acid were dissolved in 25 parts by volume of acetic acid, and 5 parts by volume of acetic anhydride were added and the mixture was stirred overnight under nitrogen. Solvent was removed under vacuum at 40°–45° C. 50 parts by volume of acetic acid were added and the evaporation repeated to form N-acetoacetyl-L-aspartic anhydride.

N-acetoacetyl-L-aspartyl-L-phenylalanine Methyl Ester

The crude anhydride was stirred with 20 parts by volume of toluene and 5 parts by volume of acetic acid. 8 parts by volume of an 0.81 Molar solution of L-phenylalanine methyl ester in toluene was added and stirred overnight. The resulting solution was evaporated under vacuum to give an oil. The oil was stirred with 50 parts by volume of ether which resulted in formation of a solid. This solid was isolated by filtration, washed with ether and air dried to give 1.61 parts of N-acetoacetyl-L-aspartyl-L-phenylalanine methyl ester as a mixture of α and β isomers.

NMR (DMSO-D6): δ 2.13, 3H, s; 2.60, 2H, m; 3.02, 2H, m; 3.35, 2H, s; 3.60, 3H, s; 4.54, 1H, m; 7.25, 5H, s; 8.30, 2H, m.

L-Aspartyl-L-phenylalanine methyl ester 1.41 parts of N-acetoacetyl-L-aspartyl-L-phenylalanine methyl ester was dissolved in 50 parts by volume of 1:1 aqueous acetic acid, 0.259 parts of hydroxylamine hydrochloride was added and the solution stirred at ambient temperatures for 4 hours to provide a mixture of α and β isomers of L-aspartyl-L-phenylalanine methyl ester.

Preparation of Disodium N-acetoacetylaspartate 8.1 parts of sodium hydroxide were dissolved in 100 parts by volume of water and the solution cooled to 0°–5° C. 13.3 parts of L-aspartic acid were added and stirred until all dissolved, then 15.8 parts by volume of diketene were added dropwise over 90 minutes, stirred at 0°–10° C. for an additional 2.5 hours, and filtered. The homogeneous solution was evaporated to dryness under vacuum at 35°–40° C. Disodium N-acetoacetylaspartate was obtained as a white foam.

Preparation of N-acetoacetyl-L-aspartyl-L-phenylalanine methyl ester

Crude disodium N-acetoacetylaspartate, 28.51 parts, was stirred with 200 parts by volume of ethyl acetate and 11.7 parts by volume of acetic acid at 0°–5° C. under argon while 4.37 parts by volume of phosphorous trichloride was added dropwise. The resulting mixture was allowed to warm to ambient temperatures while stirring for 20 hours. To the resulting solution which contains N-acetoacetyl-L-aspartic anhydride was added dropwise over a 2 hour period 122 parts by volume of 0.9M L-phenylalanine methyl ester in dioxane. After continued stirring for 20 hours, the solvent was evaporated under vacuum at 35°–40° C. Toluene, 200 parts by volume, was added to the residue and the evaporation was repeated, giving crude N-acetoacetyl-L-aspartyl-L-phenylalanine methyl ester as a semi-solid yellow residue.

L-aspartyl-L-phenylalanine methyl ester hydrochloride dihydrate

The crude N-acetoacetyl-L-aspartyl-L-phenylalanine methyl ester was dissolved in 100 parts by volume of water and 11.7 parts by volume of acetic acid. Toluene 200 parts by volume and 6.95 parts of hydroxylamine hydrochloride were added and the mixture stirred for 2.5 hours. The aqueous layer was separated and cooled to 0°–5° C. 15 parts by volume concentrated hydrochloric acid were added and the resulting mixture was cooled at 0°–5° C. overnight. The precipitate was collected on a filter and air dried for 3 hours to give 26.4 parts of α-L-aspartyl-L-phenylalanine methyl ester hydrochloride dihydrate.

α-L-aspartyl-L-phenylalanine methyl ester 12.5 parts of α-L-aspartyl-L-phenylalanine methyl ester hydrochloride dihydrate was dissolved in 100 parts by volume of water and aqueous sodium carbonate added to pH3, then heated to 60° C. and adjusted to pH4.6. The reaction mixture was cooled to 5° C. for three hours and the precipitate was collected on a filter and dried for 18 hours under vacuum at 60° C. to give 7.6 parts α-L-aspartyl-L-phenylalanine methyl ester.

Isolation and characterization of N-acetoacetyl-L-aspartic anhydride 2.0 parts of sodium hydroxide were dissolved in 25 parts by volume of water and cooled to 0°–10° C. Then 3.33 parts L-aspartic acid were added and the mixture stirred until all dissolved. To this mixture was added 3.95 parts by volume of diketene dropwise while maintaining temperature and continued stirring for 3 hours. The solvent was evaporated from the homogeneous solution under vacuum at 35°–40° C. until the mixture began to foam. 25 parts by volume of acetic acid was added and evaporation was repeated. This process was repeated twice to give 20.7 parts of clear solution. To this clear solution was added 12.5 parts by volume of ethyl acetate and 4.7 parts by volume of acetic anhydride. After about 1 hour a thick precipitate formed and stirring was continued for 18 hours. The solid was isolated by filtration, washed twice with 10 parts by volume of cold ethyl acetate and dried under vacuum at 35°–40° C. for 24 hours to give 9.85 parts of anhydride contaminated with sodium acetate/acetic acid. This material was stirred with 100 parts by volume of dioxane for 5 hours. After filtration to remove remaining solid, the dioxane was evaporated under vacuum at 35°–40° C. and the residue was dried under vacuum at the same temperature for 24 hours to give 1.08 parts of N-acetoacetyl-L-aspartic anhydride, mp 131.5°–135° C.:

Elemental analysis for $C_8H_9NO_5$ Calc. C, 48.25; H, 4.55; N, 7.03. Found C, 48.42; H, 4.50; N, 6.72.

NMR (Dimethylformamide-D7) δ 2.23, 3H, s; 2.8–3.7, 2H, AB portion of ABX; 3.53, 2H, s; 4.99, 1H, m; 9.04, 1H, m.

Preparation and isolation of N-acetoacetyl-α-L-aspartyl-L-phenylalanine methyl ester 4.5 parts of diketene were added dropwise to a stirred suspension of 14.7 parts α-L-aspartyl-L-phenylalanine methyl ester in 400 parts by volume of tetrahydrofuran and stirred for 20 hours at ambient temperatures. An additional 4.2 parts of diketene was added. After 18 hours, the solvent was removed under vacuum and the residue was purified by chromotography on silica gel to give N-acetoacetyl-α-L-aspartyl-L-phenylalanine methyl ester, mp 118.5°–121° C. which eluted in a 10:90:0.1 ethanol:methylene chloride:acetic acid mixture.

Elemental analysis for $C_{18}H_{22}N_2O_7$: Calc. C, 57.14; H, 5.86; N, 7.40. Found C, 56.91; H, 5.80; 7.31.

NMR (Dimethyl sulfoxide-D6): δ 2.13, 3H, s; 2.59, 2H, m; 3.02, 2H, m; 3.35, 2H, s; 3.60, 3H, s; 4.53, 2H, m; 7.24, 5H, s: 8.30, 2H, m.

N-Acetoacetyl-L-aspartic anhydride 21.72 parts of N-acetoacetyl-L-aspartic acid, 0.14 parts of magnesium acetate, and 9.5 parts by volume of acetic anhydride were mixed with 200 parts by volume of ethyl acetate and heated at 55±2° C. under argon for 24 hours.

N-acetoacetyl-L-aspartyl-L-phenylalanine methyl ester

To the above mixture was added 60 parts by volume of a 1.67M solution of L-phenylalanine methyl ester in ethyl acetate over 90 minutes. The resulting solution was stirred at ambient temperatures for 2 hours.

α-L-Aspartyl-L-phenylalanine methyl ester

To the above solution was added 260 parts by volume of hexane, 336 parts by volume of water, 1.65 parts by volume of concentrated hydrocholoric acid, and 6.95 parts of hydroxylamine hydrochloride. The resulting two-phase mixture was stirred at ambient temperatures for 2 hours. The aqueous layer was drawn off and treated with sodium carbonate to bring to pH 3.0. The solution was heated to 60° C. and sodium carbonate was again added to bring to pH 4.6. The solution was allowed to cool to 24° C. and was then stored at 0°–5° C. overnight. The precipitate was removed by filtration, washed with 75 parts by volume of cold water and pulled dry for 30 minutes, then dried under vacuum at 60° C. overnight to give 14.3 parts α-L-aspartyl-L-phenylalanine methyl ester.

N-acetoacetyl-L-aspartic anhydride 2.17 parts of N-acetoacetyl-L-aspartic acid, 1.02 parts by volume of acetic anhydride, and 0.014 parts of magnesium acetate were mixed with 40 parts by volume of ethyl acetate and heated at 55±2° C. under nitrogen for 24 hours. 30 parts by volume of methanol was added and the mixture stirred at ambient temperatures for 5 hours. HPLC analysis of the resulting solution showed only 0.5% unreacted N-acetoacetyl-L-aspartic acid.

N-acetoacetyl-L-aspartic acid in methanol

Potassium hydroxide (90%), 49.9 parts, was dissolved in 250 parts by volume of methanol and the resulting solution was cooled to 25° C. L-aspartic acid, 53.2 parts, was added with good stirring and the resulting solution was cooled to 0° C. with a dry-ice-alcohol bath. Diketene, 35.2 parts, was added during about 20 minutes while maintaining the temperature at about −4° to 0° C. The solution was stirred at 0° C. for an additional 10 minutes and then was allowed to warm to 10°–15° C. Phosphoric acid (85%), 54.5 parts by volume, was added with continued stirring and cooling, the temperature being maintained at 10°–15° C. The mixture was stirred for an additional 30 minutes and then was filtered. The solid potassium dihydrogen phosphate was rinsed with about 200 parts by volume of methanol and the filtrates were combined. Methanol was distilled from the filtrate at a vacuum of 25–50 mm Hg to leave a syrup containing N-acetoacetyl-L-aspartic acid and water. Water was removed from the product by evaporation under a higher vacuum (<1 mm Hg) at about 70° C. to leave a solid residue of 84.6 parts of N-acetoacetyl-L-aspartic acid.

N-acetoacetyl-L-aspartic acid

L-aspartic acid, 53.2 parts, was slurried with 120 parts by volume of water and 41.1 parts by volume of 51.6% aqueous sodium hydroxide solution was added with stirring and cooling. The resulting solution was cooled to 0°–10° C. and 20 parts by volume of 2-butanone was added. Diketene, 35.2 parts, was added during about 20 minutes while maintaining the temperature at about 10° C. The mixture was stirred at about 10° C. for an additional 10 minutes and then was allowed to warm to 15°–20° C. Additional 2-butanone, 80 parts by volume, was added and the mixture was acidified by addition of 22.2 parts by volume of concentrated sulfuric acid. The temperature of the mixture was allowed to rise to 40°–45° C. to prevent crystallization of sodium sulfate. The 2-butanone layer was separated and the aqueous layer was extracted three times with 50 parts by volume portions of 2-butanone; the mixture was maintained at a temperature of 35°–40° C. during these extractions. The combined extracts were dried over sodium sulfate, filtered, and the 2-butanone was distilled under a vacuum of 24–30 mm Hg to leave a syrup containing water and N-acetoacetyl-L-aspartic acid. Water was removed from the product by evaporation under a higher vacuum (<1 mm Hg) at about 70° C. to leave a solid residue of about 79.4 parts of N-acetoacetyl-L-aspartic acid.

What is claimed is:
1. N-acetoacetyl-L-aspartic acid.
2. N-acetoacetyl-L-aspartic anhydride.

* * * * *